United States Patent
Papiorek

(10) Patent No.: US 10,159,787 B2
(45) Date of Patent: Dec. 25, 2018

(54) PORT CANNULA SYSTEM FOR PUNCTURING PORT CATHETERS

(71) Applicant: Fresenius Kabi Deutschland GmbH, Bad Homburg (DE)

(72) Inventor: Martina Papiorek, Hünfelden (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 459 days.

(21) Appl. No.: 14/408,643

(22) PCT Filed: Jun. 18, 2013

(86) PCT No.: PCT/EP2013/062598
§ 371 (c)(1),
(2) Date: Dec. 17, 2014

(87) PCT Pub. No.: WO2013/189918
PCT Pub. Date: Dec. 27, 2013

(65) Prior Publication Data
US 2016/0015891 A1    Jan. 21, 2016

Related U.S. Application Data

(60) Provisional application No. 61/660,986, filed on Jun. 18, 2012.

(30) Foreign Application Priority Data

Jun. 18, 2012  (EP) .................................... 12172480

(51) Int. Cl.
   *A61M 5/158*   (2006.01)
(52) U.S. Cl.
   CPC ..... *A61M 5/158* (2013.01); *A61M 2005/1586* (2013.01)

(58) Field of Classification Search
   CPC .......... A61M 5/158; A61M 2005/1581; A61M 2005/1586
   (Continued)

(56) References Cited

U.S. PATENT DOCUMENTS

| | | |
|---|---|---|
| 4,769,010 A | 9/1988 | Fenton, Jr. et al. |
| 5,951,522 A | 9/1999 | Rosato et al. |

(Continued)

FOREIGN PATENT DOCUMENTS

| | | |
|---|---|---|
| DE | 102008052787 | 4/2010 |
| EP | 0769302 | 4/1997 |

(Continued)

*Primary Examiner* — Kevin C Sirmons
*Assistant Examiner* — Leah Swanson
(74) *Attorney, Agent, or Firm* — Occhiuti & Rohlicek LLP

(57) ABSTRACT

A port cannula system for puncturing implantable and implanted port catheters comprises a cannula holder, a cannula secured on the cannula holder and having a cannula tip. The cannula tip can be moved to at least one of a puncture position and a safety position. The port cannula system further includes a feeder connected to the cannula, and at least one support piece connected to the cannula holder for supporting the port cannula system on a patient's skin. The support piece is connected to the cannula holder by a hinge. The hinge permits height compensation, for example, if the patient's skin is not flat in the area of application or if the patient moves. The support piece, in conjunction with the hinge, thus represents a kind of leveling element.

22 Claims, 9 Drawing Sheets

(58) Field of Classification Search
USPC .................................. 607/174, 177, 180
See application file for complete search history.

(56) References Cited

U.S. PATENT DOCUMENTS

| | | | | |
|---|---|---|---|---|
| 6,926,693 | B2* | 8/2005 | Enns | A61M 5/158 604/165.03 |
| 2004/0087912 | A1* | 5/2004 | Swenson | A61M 5/3216 604/263 |
| 2005/0107749 | A1* | 5/2005 | Smith | A61M 5/158 604/263 |
| 2005/0251098 | A1* | 11/2005 | Wyss | A61M 5/158 604/263 |
| 2007/0078432 | A1* | 4/2007 | Halseth | A61M 5/158 604/500 |
| 2007/0161953 | A1* | 7/2007 | Chawki | A61M 5/158 604/116 |
| 2008/0243084 | A1* | 10/2008 | DeStefano | A61M 5/158 604/180 |
| 2009/0299302 | A1 | 12/2009 | Lambert | |

FOREIGN PATENT DOCUMENTS

| | | |
|---|---|---|
| EP | 2404547 | 1/2012 |
| WO | 1999/015221 | 4/1999 |
| WO | 2009/055739 | 4/2009 |
| WO | 2010/142641 | 12/2010 |

* cited by examiner

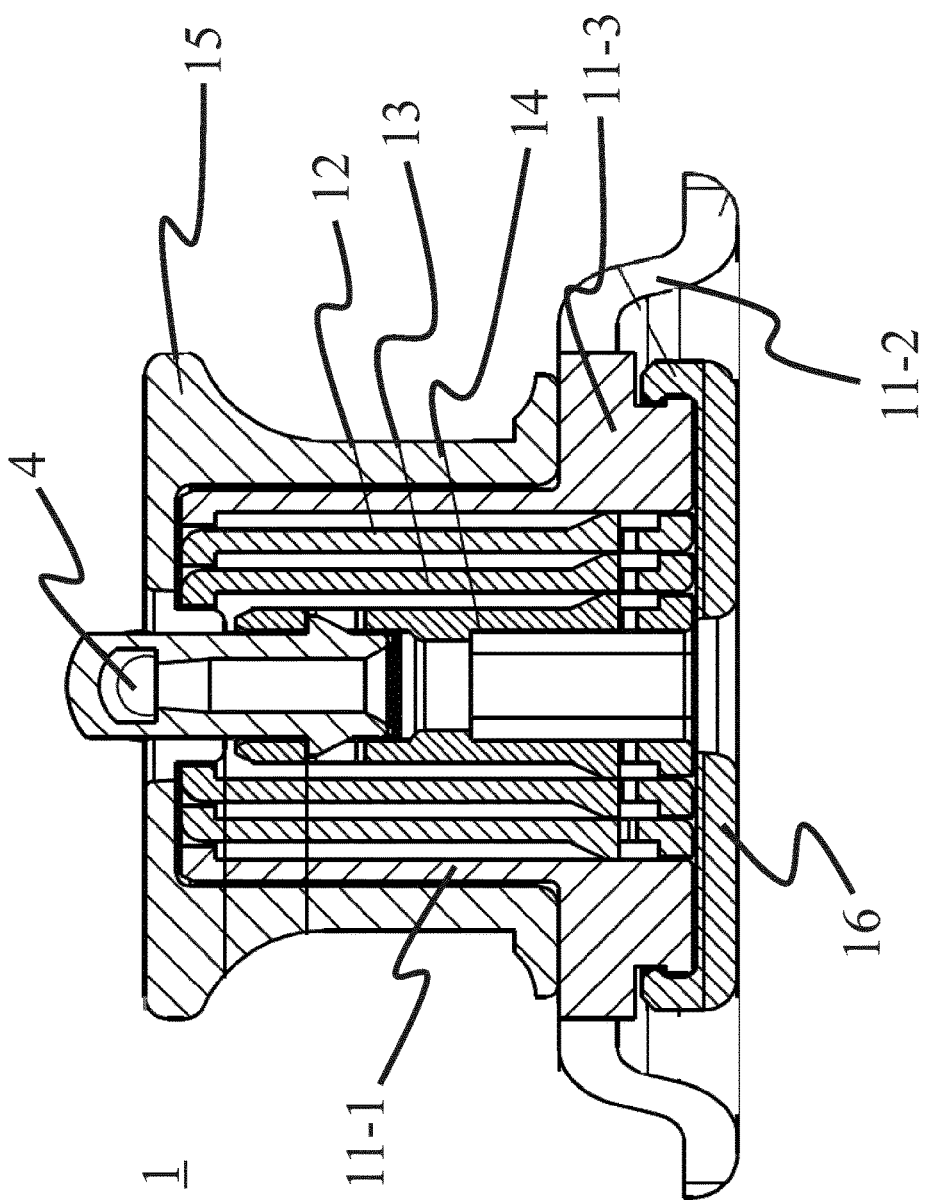
Fig. 1.a

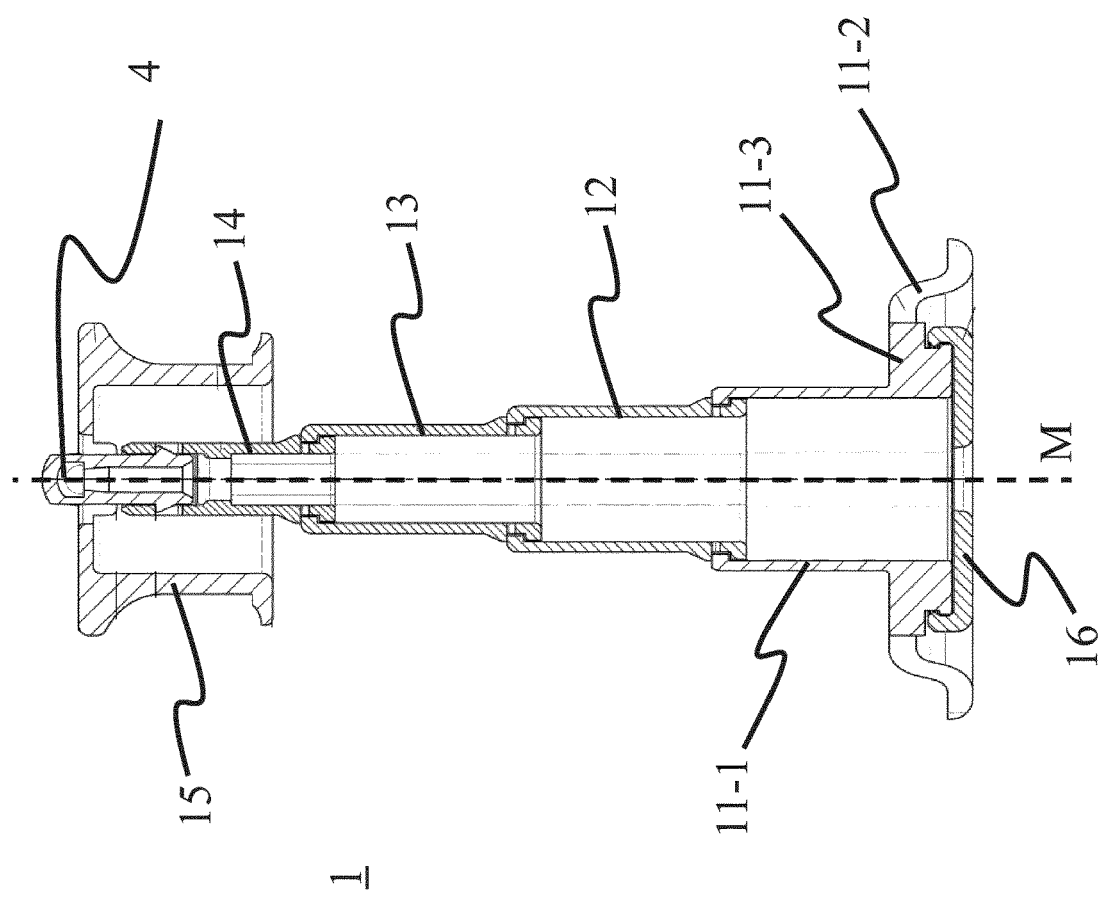
Fig. 1.b

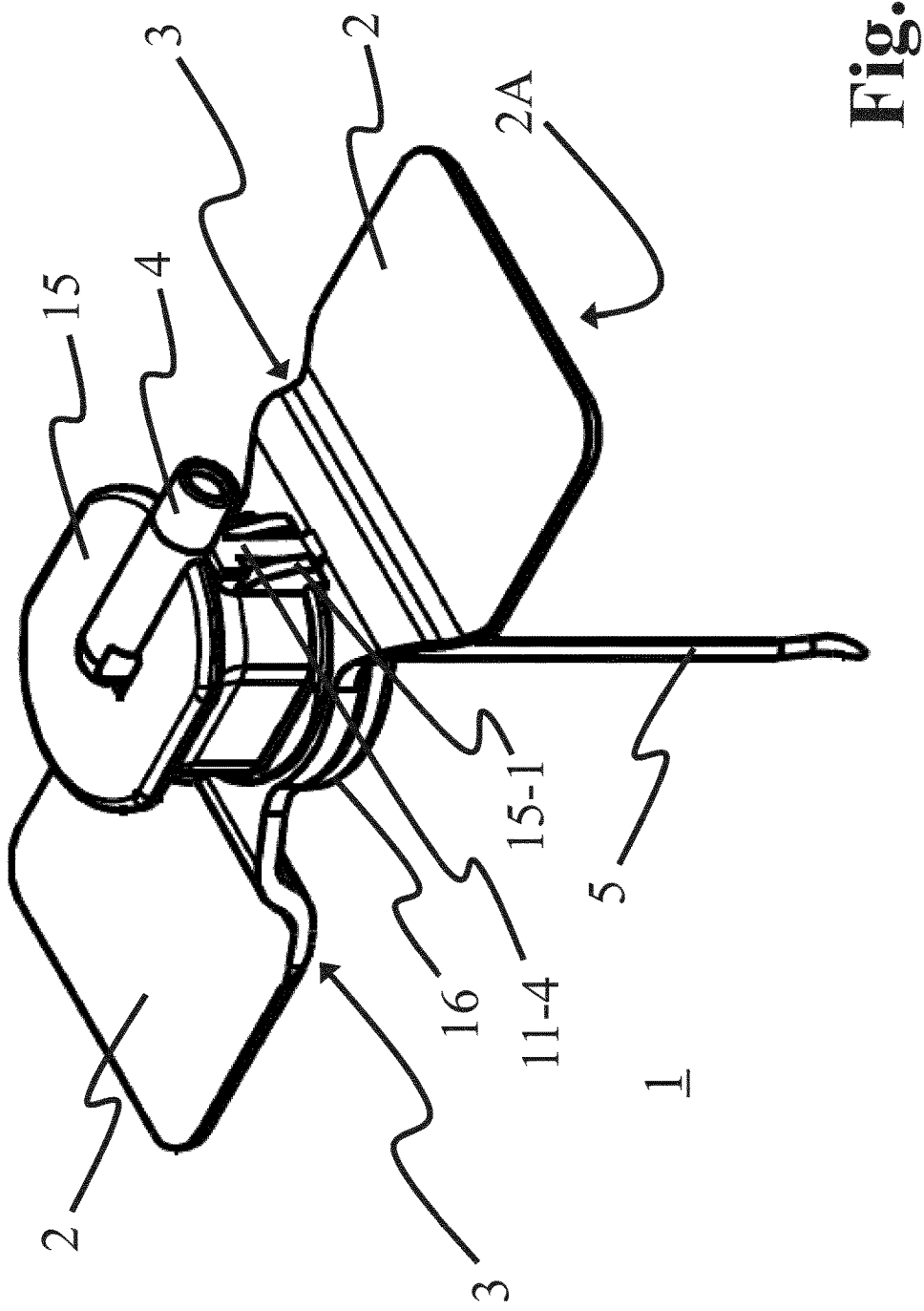

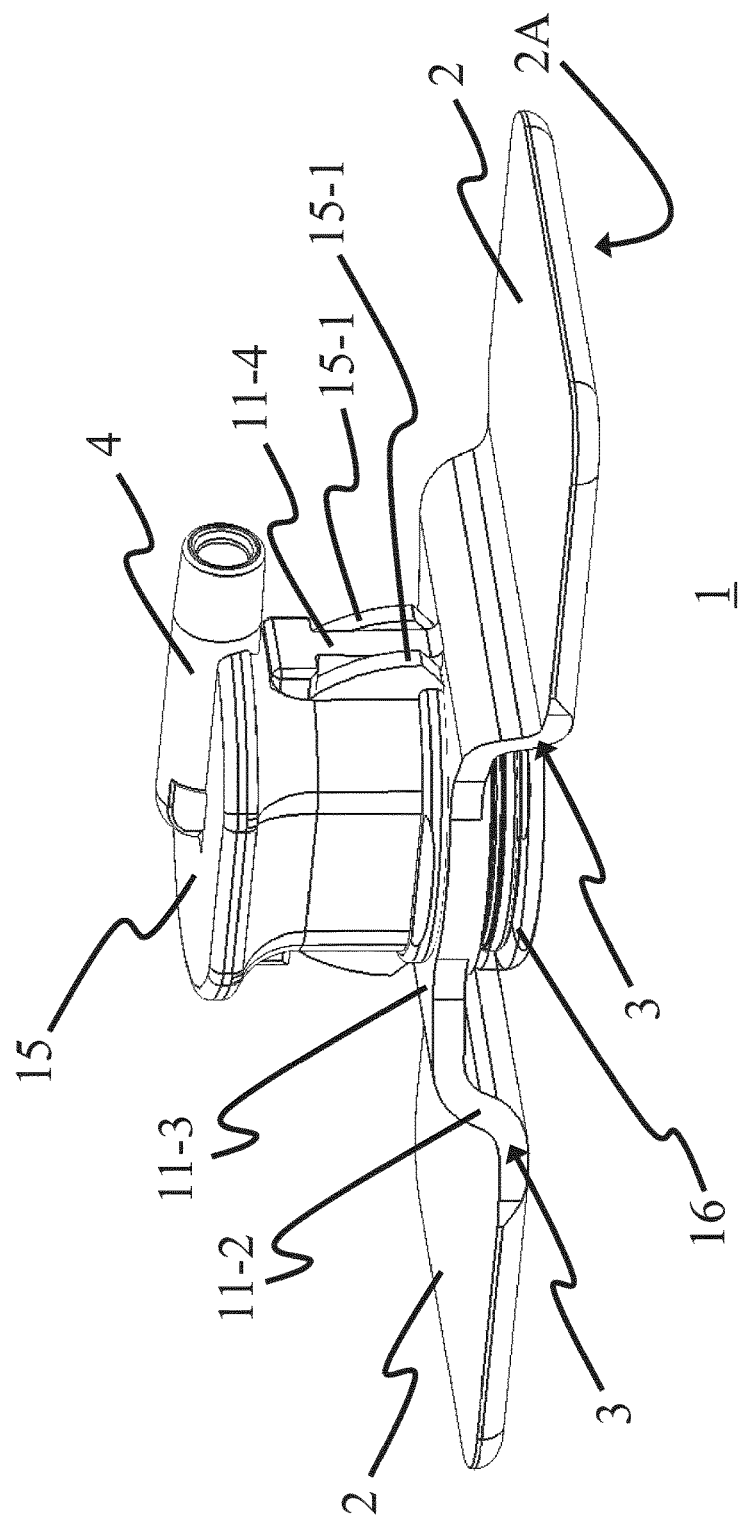

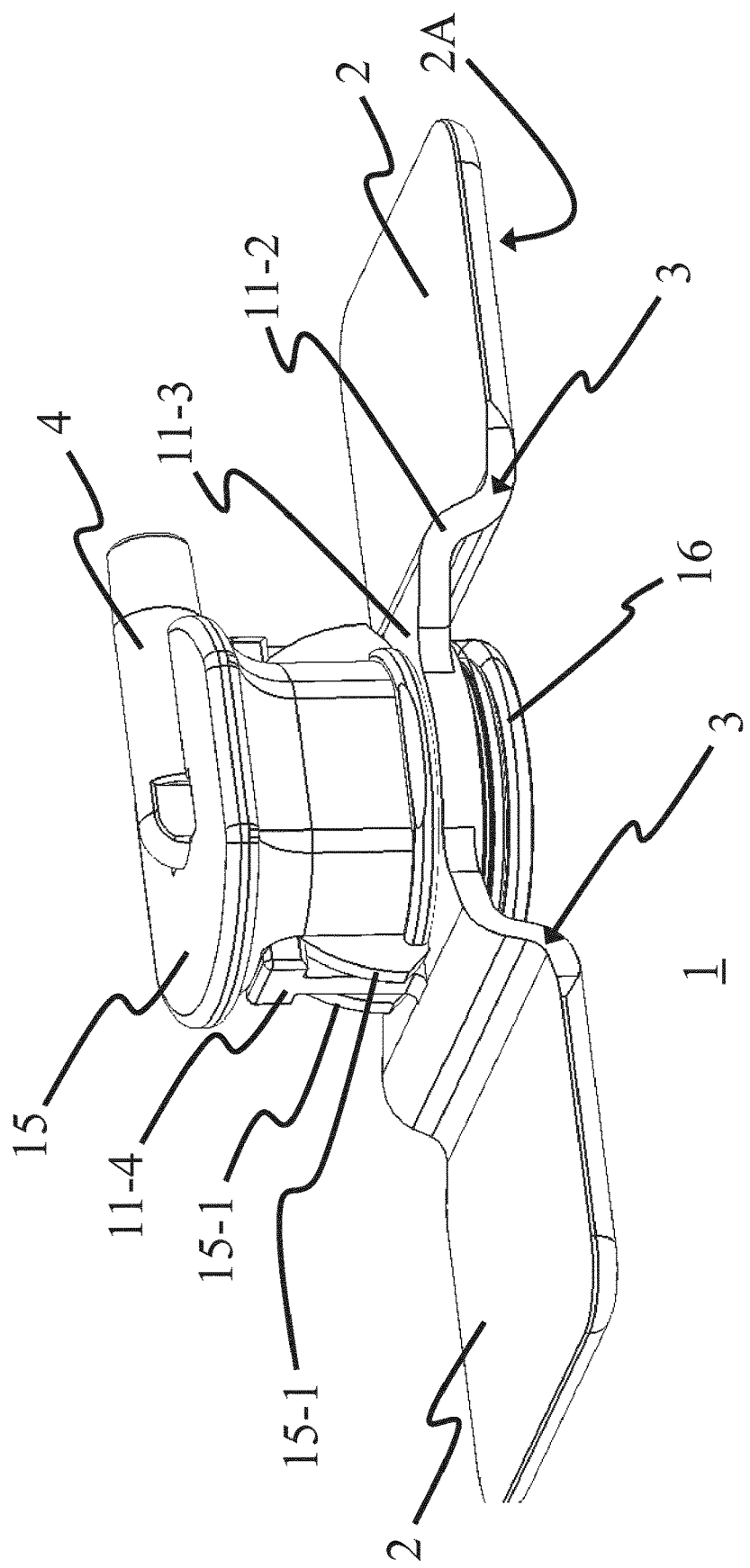
Fig. 3.b

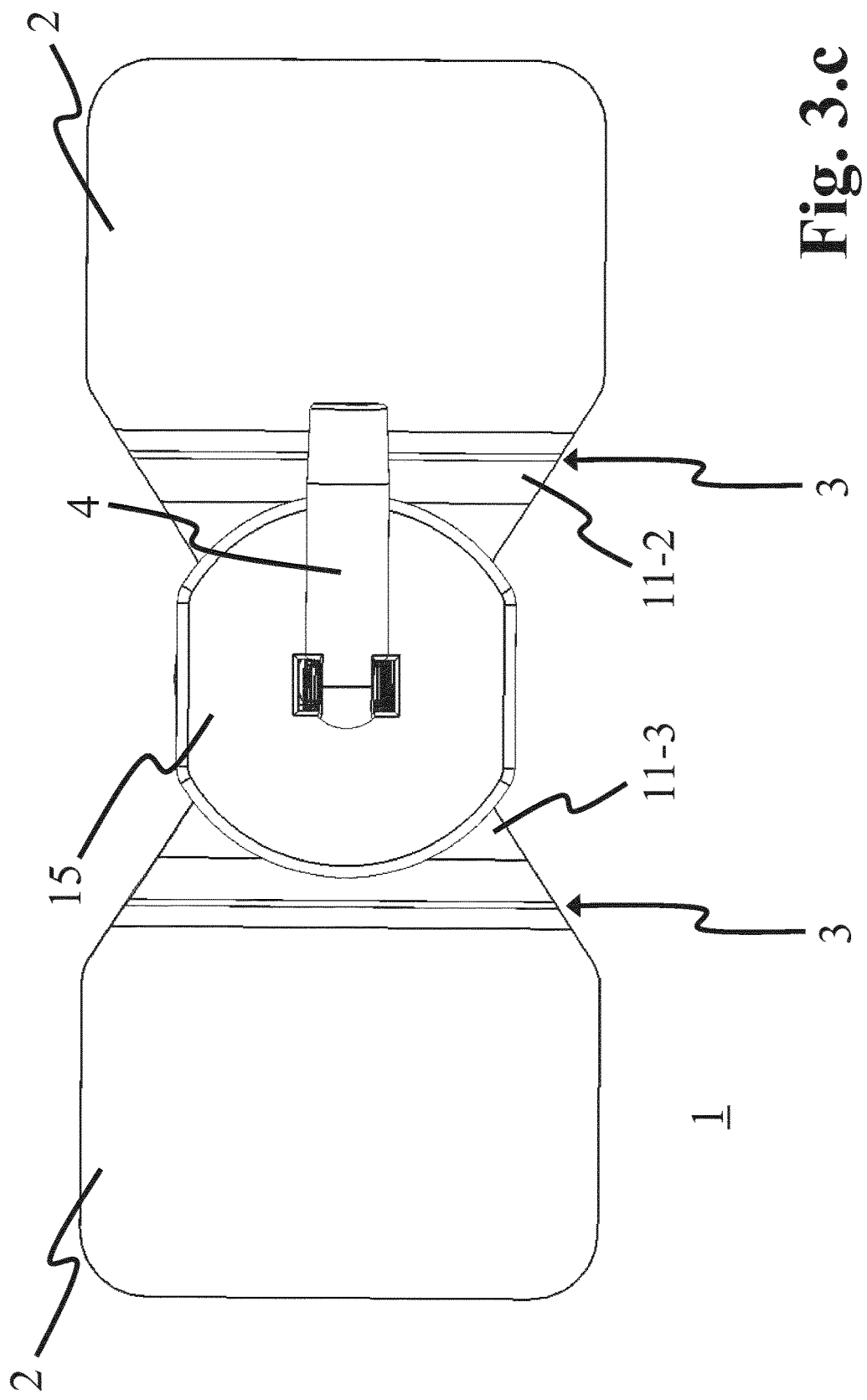
Fig. 3.c

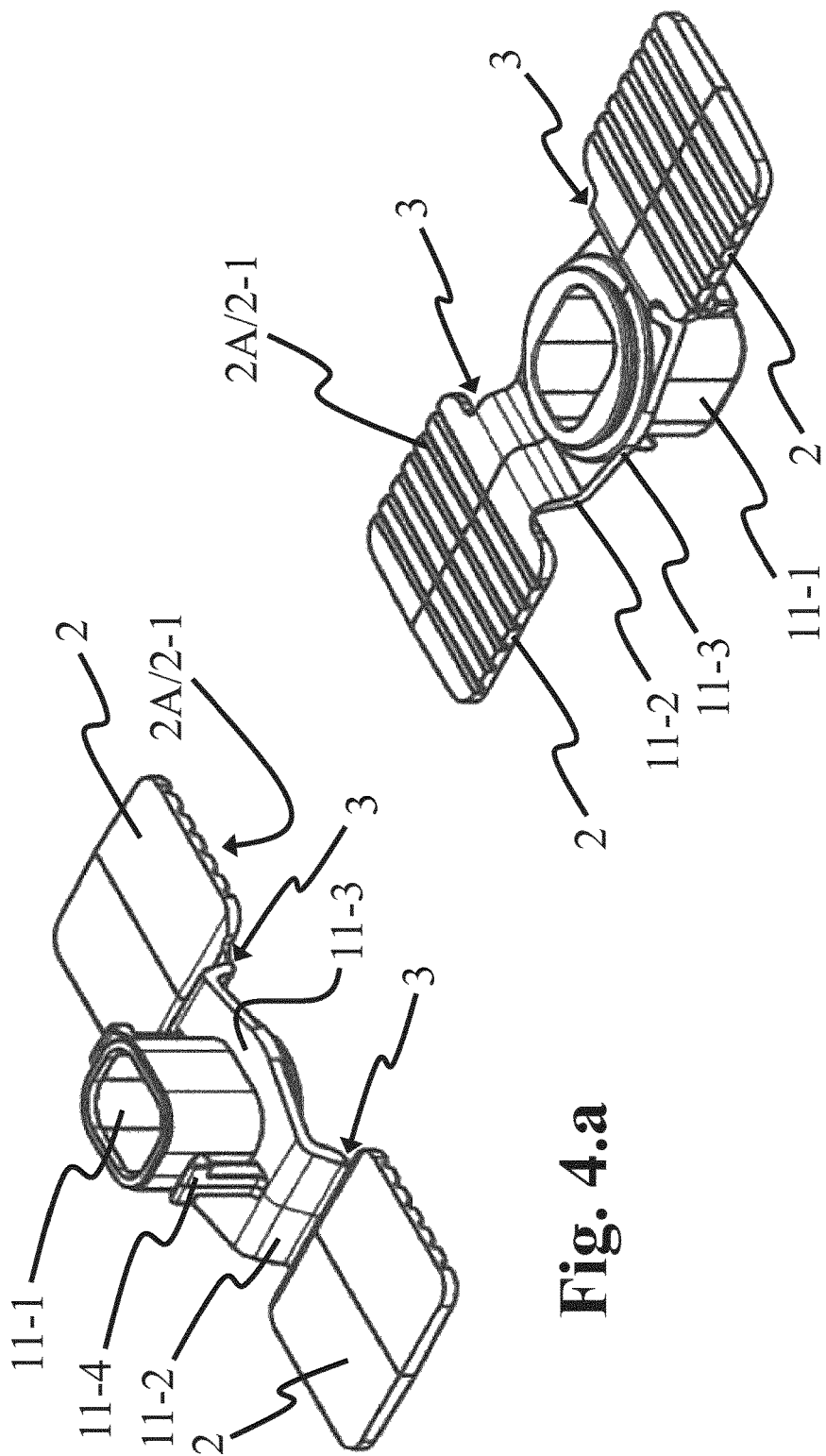

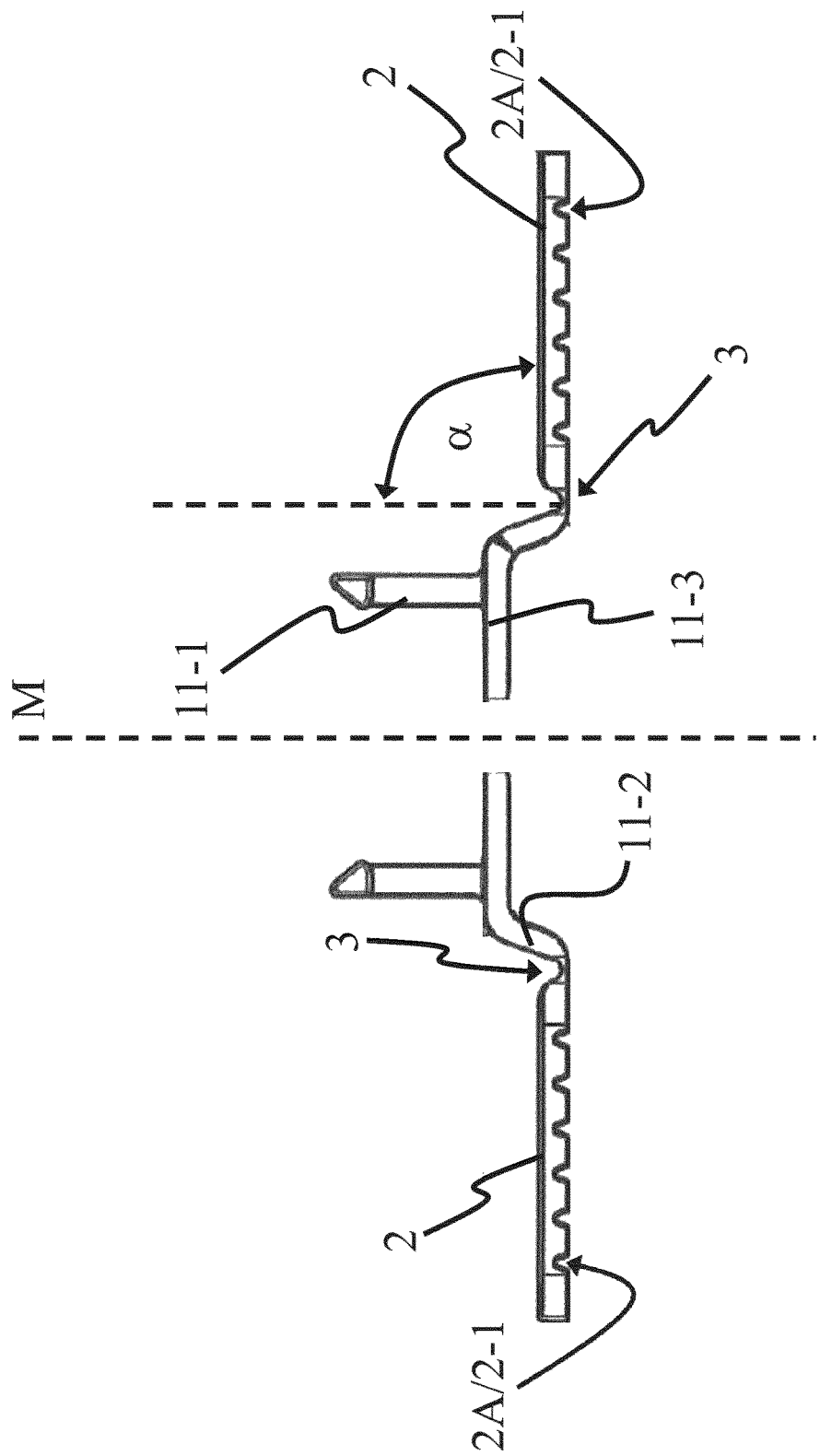

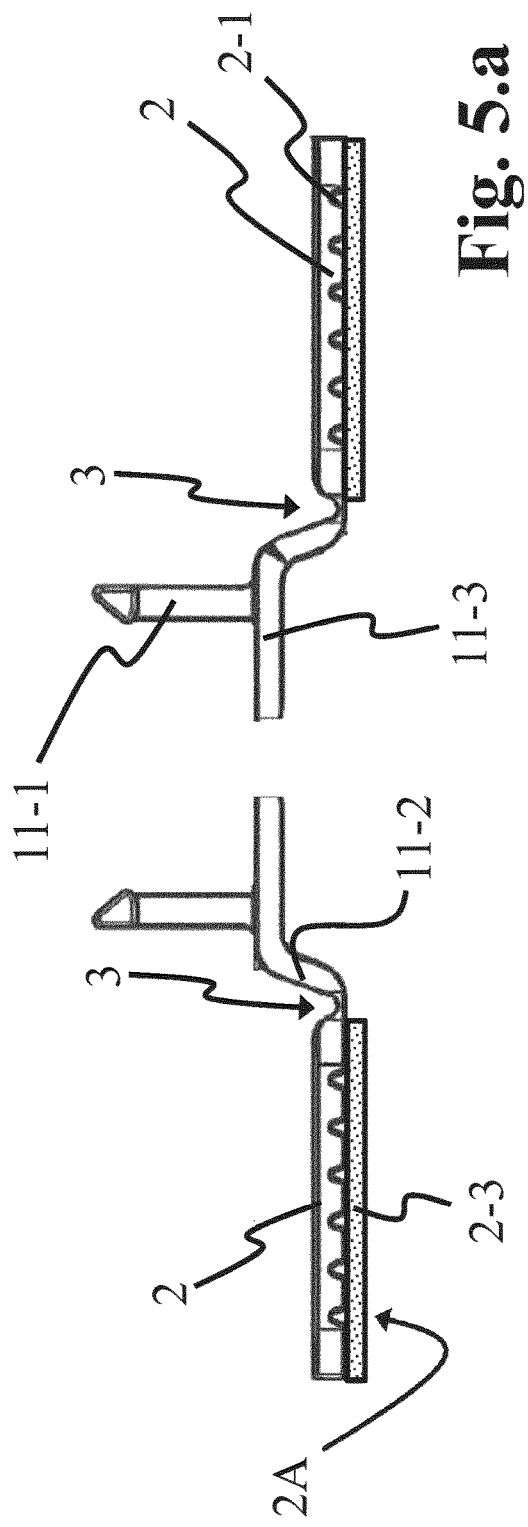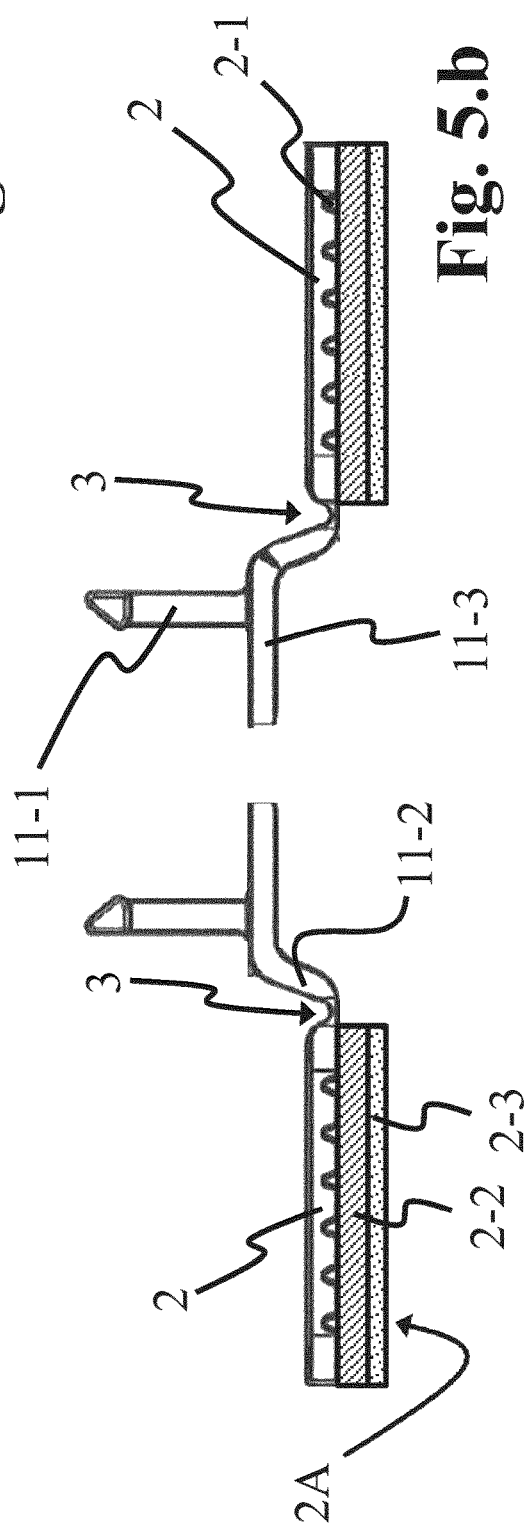

PORT CANNULA SYSTEM FOR PUNCTURING PORT CATHETERS

The present invention relates to port cannula systems for puncturing implantable and implanted port catheters.

BACKGROUND OF THE INVENTION

Many port cannula systems are disclosed in the prior art and are used to establish a connection to a port implanted in the human or animal body. Such ports are implanted in order to permit simpler and more reliable introduction of substances into the human body, in particular into the central vessels thereof.

For the connection to a port, the port cannula system has a cannula with a cannula tip. Such a cannula tip is dangerous and is therefore generally enclosed, in the supply state, by a cannula guard, e.g. in the form of a sleeve that can be fitted on the cannula. The cannula guard is removed shortly before application of the port cannula. Although the cannula is sterile at this point and does not pose a risk of infection, it nonetheless poses a risk of injury to the user.

By contrast, when the port cannula system is withdrawn from the patient or from the port within the patient, the cannula is no longer sterile and thus not only poses a risk of injury but also a high risk of infection, not only to the medical personnel but also to the staff of the waste management business. For this reason, it is desirable to equip port cannula systems with a needlestick protection device, which in particular provides protection against needlestick injuries during and after withdrawal of the port cannula system after use.

A port cannula system with an efficient needlestick protection device is described, for example, in the document WO 2010/142641 A1. The entire content of this document is incorporated by reference into the present patent application. The port cannula system has the following components: a support piece for supporting the port cannula on the patient, a feeder, a cannula with a tip, wherein the cannula can be brought to at least two positions, namely a puncture position and a retracted protection position, and a safety portion which screens the tip of the cannula at least in the retracted position and thus forms a needlestick protection device. The safety portion is formed by telescope segments which are pushed substantially into one another in the puncture position and are drawn farther apart from one another in the retracted position (in this connection see also FIGS. 5.a and 5.b of the present application). The safety demands placed on a port cannula system are satisfied to a great extent by the port cannula system as described in WO 2010/142641 A1. The port cannula system comprises an integrated plaster which has a large surface area and which completely encloses the cannula holder, and an integrated leveling element for securing on a large surface area of a patient's skin. The port cannula system described there is particularly suitable for users who wish to secure the port cannula system quickly and easily after the puncture and whose patients do not need a daily change of dressing.

GENERAL DESCRIPTION OF THE INVENTION

Against the background outlined above, an object of the present invention is to make available an alternative port cannula system. In particular, the port cannula system is intended to be easier to produce.

The objects are already achieved by the port cannula system according to independent patent claim 1. Advantageous embodiments of the port cannula system according to the invention are the subject matter of the dependent claims.

The present invention is described on the basis of a port cannula system comprising the following components: a cannula holder, a cannula secured on the cannula holder and having a cannula tip, which can be moved at least to a puncture position and a safety position, a safety portion which at least partially surrounds the cannula tip in the safety position, a feeder connected to the cannula, and at least one support piece connected to the cannula holder for supporting the port cannula system on a patient's skin, wherein the at least one support piece is connected to the cannula holder by a hinge.

The support piece forms the support surface with which the port cannula system is placed on the patient's skin. It is a kind of carrier for the port cannula system. For example, the support piece has a support surface measuring approximately 5 mm to 30 mm by 5 mm to 30 mm, preferably 10 mm to 20 mm by 10 mm to 20 mm. The thickness of the support piece measures approximately 0.5 to 4 mm, preferably 1 mm to 2 mm. The support piece is secured movably on the port cannula system or the cannula holder by way of the hinge. The hinge permits height compensation if, for example, the patient's skin is not flat in the area of application or if the patient moves. The support piece, in conjunction with the hinge, thus represents a kind of leveling element.

The support piece does not constitute a device for gripping the port cannula system, by means of which device the port cannula system can be gripped and can be removed from a patient's skin. Therefore, when used as intended, the support piece cannot be folded or pivoted upwardly, for example by at least 90° upward or relative to a horizontal. The pivot range of the support piece about an axis defined by the hinge is smaller. This is because the hinge is intended mainly to permit only a height compensation, so as to permit a defined placement of the port cannula system on uneven skin, for example. In one embodiment, the support piece is pivotable, about an axis formed by the hinge, in an angle range α of 0°<α≤270°. The angle α is defined by the angle which is enclosed between the longitudinal axis of the port cannula system and the support piece, in particular the top face of the support piece.

In a preferred embodiment of the invention, the hinge is a preferably linear film hinge. Such a configuration is easy to produce. In particular, the limited pivot range of the support piece can be set by the dimensions of the film hinge.

In particular, the film hinge has, at its thinnest point, a thickness which is reduced by a factor of less than a half, preferably less than a third, compared to the thickness of the support piece. In one embodiment, the film hinge has, at its thinnest point, a thickness in a range of 0.1 mm to 1 mm, preferably of 0.2 mm to 0.6 mm. The radius of curvature of the recess or thinning that forms the film hinge lies in a range of 0.1 mm to 1 mm, preferably of 0.3 mm to 0.7 mm.

In particular, the support piece is formed by at least two plates, which extend laterally outward from the cannula holder. The two plates are preferably arranged lying opposite each other. In this configuration, the two plates form a kind of wing arrangement. The two plates or wings are each connected by a respective hinge to the cannula holder.

The cannula holder carries the cannula directly or indirectly. It is preferably constructed in several parts. In one embodiment, it comprises a lower holder segment which is connected to the support piece and which forms a step, such that, when the port cannula system is placed on the patient's skin, the lower holder segment and therefore also the cannula holder as a whole are at a distance from the patient's skin. A space is formed between the underside of the cannula holder and the patient's skin. The lower holder segment of the cannula holder forms toward the side a step which, at its lowest point, adjoins the support piece. The hinge is situated between the step and the support piece. The hinge connects the step of the lower holder segment to the support piece. The space formed under the system by the step permits better observation of the puncture site. Better observation is generally ensured by daily change of dressing, for which purpose a compress is placed underneath the port cannula system. Secretions can be detected on this compress during a change of dressing.

In particular, the support piece and/or the cannula holder are produced by injection molding. A preferred material for the support piece and/or the cannula holder is polypropylene. Particularly in the embodiment in which the hinge is designed as a film hinge, at least the lower holder segment of the cannula holder and the support piece are made integrally. A single part is thus provided that can be produced in one manufacturing step and therefore in a cost-effective manner.

In one possible embodiment of the support piece, a large number of grooves are formed on at least parts of the underside of the support piece. These grooves permit a high degree of flexibility of the support piece. Moreover, they ensure air circulation and, therefore, a reduction of the moisture development by skin contact in the case of a partial skin padding geometry.

In a further embodiment, a padding or support piece padding is arranged on at least parts of the underside of the support piece. The wearing comfort of the port cannula system for the patient can thereby be increased. Possible materials for the padding or support piece padding are viscose/polypropylene and/or a polyether sulfone/polyethylene mixture and/or a polyethylene/polyurethane mixture (in particular as wound cushion) and/or a polyester nonwoven (in particular as wound and/or skin dressing) and/or a preferably transparent polyethylene film (in particular as skin dressing) and/or a polyethylene foam (in particular as skin dressing padding), preferably in each case combined and/or coated with an adhesive, for example a polyacrylate adhesive. The support surface of the padding can substantially correspond to the support surface of the support piece according to the invention. The padding has, for example, a thickness in a range of 0.1 mm to 3 mm, preferably of 0.5 mm to 1.5 mm.

In an alternative or supplementary embodiment, an underside of the support piece and/or of the padding is covered at least in parts with a layer of an adhesive for releasably connecting the support piece to the patient's skin. This permits simple and reliable securing of the system on the skin of a patient. To prevent the adhesive from drying out, the adhesive is generally covered with a peel-off film. In addition, the port cannula system can also be secured with one or two separate adhesive tapes.

As has already been explained above, the cannula can be brought to at least two positions, namely a puncture position and a preferably retracted safety position. In the puncture position, the cannula or at least the cannula tip lies free in order to penetrate an implanted port. In the puncture position, the safety portion frees at least part of the cannula or at least the cannula tip. In the safety position, the cannula or at least the cannula tip is retracted to a position or placed in a position in which it is screened off and, for example, cannot injure a user. For this purpose, the safety portion is provided which surrounds or screens off the cannula tip at least in the preferably retracted position and thereby forms a needlestick protection device. In the safety position, the cannula or at least the cannula tip is positioned, preferably centrally, in an inner space formed by the safety portion. The safety portion is connected to the cannula holder. In particular, the safety portion can be pulled out, preferably along its longitudinal axis, to provide the safety position. The safety portion can also be designated as a needlestick protection device.

In one embodiment of the cannula holder, the latter has at least one middle holder segment connected to the lower holder segment, and an upper holder segment connected to the middle holder segment. Moreover, the cannula holder can have a grip piece for operating the port cannula system, which grip piece is preferably connected to the upper holder segment. In particular, the feeder is secured on the cannula holder, in particular on the grip piece.

In a preferred embodiment of the present invention, the upper holder segment, the at least one middle holder segment and/or the lower holder segment are telescope segments, which are movable relative to one another and are guided with respect to one another, wherein the telescope segments are pushed at least partially into one another in the puncture position and are drawn further apart from one another in the retracted protection position. In the safety position, at least the cannula holder is screened off by said telescope segments. In this variant of the invention, the telescope segments form the safety portion. The cannula and the cannula tip are arranged in the inner space formed by the telescope segments.

In one embodiment, the cannula holder, the support piece, the feeder, the lower holder segment, the middle holder segment, the upper holder segment, the grip piece, the padding, the adhesive for the padding and/or the adhesive for connection to the skin is/are formed by a transparent material or substantially transparent material, in particular a transparent plastic. Preferably, all the components of the port cannula system are formed by a transparent material. For example, when a wall of a component is placed onto a white sheet of paper printed with numbers in black, the printed numbers can be seen through the wall. This ensures improved observation and monitoring of the puncture site and of the area around the latter.

Moreover, the present invention also relates to a kit comprising a port cannula system with the properties described above, an adhesive tape for securing the port cannula system on a patient's skin, a compress for positioning between the port cannula system and the patient's skin, a needle protection cap that can be mounted or is mounted on the cannula, a hose that is connected or can be connected to the feeder, a hose clamp and/or a connector that is connected or can be connected to the hose, in particular a female Luer lock connector.

The present invention is explained in detail on the basis of the following illustrative embodiments. Reference is made to the attached drawings. The same reference signs in the individual drawings relate to the same parts.

FIGS. 1.*a* and 1.*b* show a schematic cross-sectional view of the port cannula system (without support piece) in its puncture position (FIG. 1.*a*) and in its retracted protection position (FIG. 1.*b*).

FIG. 2 shows a schematic perspective view of the upper face of a port cannula system according to the invention (with cannula).

FIGS. 3.a to 3.c show schematic views of a port cannula system according to the invention (without cannula) in two perspective views (FIGS. 3.a and 3.b) and in a plan view (FIG. 3.c).

FIGS. 4.a to 4.c show different schematic views of a one-part cannula holder with two support pieces, in a perspective view of the top face (FIG. 4.a) and of the underside (FIG. 4.b) and in a cross section (FIG. 4.c).

FIGS. 5.a to 5.b show schematic views of two embodiments of the cannula holder from FIG. 4.c with an adhesive layer applied to the underside of the support pieces (FIG. 5.a) and a padding with an adhesive layer (FIG. 5.b).

The present invention is illustrated using the example of a port cannula system 1 that includes a needlestick protection device as described in WO 2010/142461 A1. The principle of the latter is essentially that the cannula 5 can be moved to at least two positions, namely a puncture position (see FIG. 1.a) and a retracted position (see FIG. 1.b), in which the tip of the cannula 5 is screened by a safety portion. The safety portion in this variant is formed by telescope segments 11-1, 12, 13 and 14, which are pushed substantially into one another in the puncture position and are drawn apart in the retracted position. FIG. 1.a illustrates the port cannula system 1 in the puncture position, in which the telescope segments 11-1, 12, 13, 14 are pushed into one another. FIG. 1.b, by contrast, illustrates the port cannula system 1 in the retracted protection position, in which the telescope segments 11-1, 12, 13 and 14 are drawn apart. The tip of the cannula 5 is screened by the telescope segments 11-1, 12, 13 and 14. When pulling out the cannula 5, the port cannula system 1 is pressed by a user onto the skin of the patient via the two support pieces 2, for example, the upper grip piece 15 is grasped and pulled upward.

FIGS. 2 to 3.c illustrate the port cannula system 1 according to the invention from different perspectives. The port cannula system 1 is formed by the following components: A cannula 5, which is carried by a cannula holder 10. The cannula holder 10 is here formed by a grip piece 15, an upper holder segment 14 connected to the grip piece 15, a first middle holder segment 13, a second middle holder segment 12, and a lower holder segment 11. The four holder segments 11, 12, 13 and 14 can be pushed into one another like a telescope. The upper holder segment 14 and the two middle holder segments 12 and 13 can therefore be designated as telescope segments. The lower holder segment 11 here comprises a lower plate 11-3, two steps 11-2 arranged laterally on the lower plate 11-3, a lower stationary telescope segment 11-1, and two clip tabs 11-4. The two clip tabs 11-4 cooperate with two slide ribs 15-1 mounted on the outside of the grip piece 15. The clip tabs 11-4 engage in the slide ribs 15-1 and form a latching connection for the puncture position. To prevent the telescope segments 12, 13 and 14 from "falling out", the port cannula system 1 also has a base plate 16, which has a through-opening for the cannula 5 and can be connected to the lower holder segment 11.

Two support pieces 2, for placing on a patient's skin, are arranged or secured on the lower holder segment 11, more precisely on the lower plate 11-3 of the lower holder segment 11. The two support pieces 2 are arranged to be movable. They constitute wings which are arranged or secured on the lower holder segment 11 of the cannula holder 10. The two support pieces 2 are connected to the cannula holder 10 by two film hinges 3.

FIGS. 4.a to 4.c show a detailed view of the two support pieces 2 and of the lower holder segment 11 of the cannula holder 10. The two support pieces 2 are connected to the lower plate 11-3 of the holder segment 11 via a step 11-2.

The step 11-2 of the lower holder segment 11 is bent at least in part. The two support pieces 2 and the lower holder segment 22 are designed here in one part. A film hinge 3 is in each case arranged or formed between the individual support piece 2 and the lower holder segment 11. The film hinge 3 is formed by a thinning in the wall thickness. A kind of groove is formed. The two wings 2 are pivotable about an axis formed by the film hinge 3. In FIG. 4.c, the pivot axis lies perpendicularly with respect to the plane of the paper. However, the two wings 2 here do not constitute wings for gripping the port cannula system 1. Instead, they constitute elements for height compensation. In this way, the port cannula system 1 can be safely positioned, for example, on a skin surface that is not flat. The fact that the wings 2 are not wings for pulling out the port cannula system 1 can be seen from the pivot range of the two wings 2. The two wings 2 are pivotable about an angle α of $0° < α ≤ 270°$ (see FIG. 4.c in this connection). The angle α is defined by the angle which is enclosed between the longitudinal axis M of the port cannula system 1 and the support piece 2. The longitudinal axis M generally runs parallel to the cannula 5 and/or is perpendicular to the plane in which the two support pieces 2 lie in the flat state. Optionally, a large number of preferably parallel grooves 2-1 or cutouts can be incorporated in the underside 2A of the two support pieces 2 (see FIGS. 4.b and 4.c).

The port cannula system 1 according to the invention provides safety functions against needlestick injuries, advantages in terms of costs, advantages to the user in terms of observing the puncture site and improved disposal, advantages to the patient in terms of freedom of movement and comfortable wearing of the port cannula system 1, in particular by comparison with systems which, although providing the same advantages in terms of size, have no movable securing elements such as a hinge.

The port cannula system 1 can be fixed on the patient's skin by means of adhesive tape, for example. Finally, FIGS. 5.a and 5.b show two further embodiments of the lower cannula holder 11. As an alternative or in addition, an adhesive layer 2-3 can be provided on the underside 2A of the support piece 2 (FIG. 5.a). In this way, the port cannula system 1 can be fixed directly on the patient's skin or at least provisionally fixed. FIG. 5.b shows a further embodiment of the lower cannula holder 10 or the support piece 2 in which a padding 2-2 is first of all applied to the underside 2A, then an adhesive layer 2-3. The wearing comfort is thereby improved.

It is clear to a person skilled in the art that the described embodiments are to be understood as examples. The invention is not limited to these and instead can be varied in many ways without departing from the concept of the invention. Features of individual embodiments, and the features mentioned in the general part of the description, can be combined with one another.

LIST OF REFERENCE SIGNS 1 port cannula system
M longitudinal axis of the port cannula system
2 support piece
2A underside of the support piece
2-1 grooves in the underside of the support piece
2-2 padding or support piece padding
2-3 adhesive layer
3 hinge or film hinge
4 feeder
5 cannula 10 cannula holder
11 lower holder segment
11-1 telescope segment of the lower holder segment
11-2 step of the lower holder segment
11-3 bottom plate of the lower holder segment
11-4 clip tabs
12 first middle holder segment or telescope segment
13 second middle holder segment or telescope segment
14 upper holder segment or upper telescope segment
15 grip piece
15-1 slide ribs on the grip piece
16 base plate

The invention claimed is:

1. A port cannula system comprising a cannula holder, a cannula secured on the cannula holder and having a cannula tip, which can be moved at least to a puncture position and a safety position, a safety portion which at least partially surrounds the cannula tip in the safety position, a feeder connected to the cannula, and at least two support pieces connected to the cannula holder for supporting the port cannula system on a patient's skin, wherein the at least two support pieces are connected to the cannula holder by at least two hinges, and wherein the cannula holder comprises a stationary one-part lower holder segment and a base plate coupled to the lower holder segment and including a through-opening through which the cannula moves, the lower holder segment comprising a plate and at least two lower holder steps extending from the plate and connected to the at least two support pieces configured to provide height compensation through pivotable movement of the at least two support pieces along the at least two hinges to allow leveling of the port cannula system on uneven regions of the patient' skin such that the through-opening of the base plate through which the cannula moves is at a distance from the patient's skin.

2. The port cannula system according to claim 1, wherein the at least two support pieces are pivotable, about an axis formed by the at least two hinges, in an angle range of $0°<\alpha<270°$ relative to a longitudinal axis of the port cannula system.

3. The port cannula system according to claim 1, wherein the at least two hinges comprise film hinges.

4. The port cannula system according to claim 1, wherein the at least two support pieces extend laterally outward from the cannula holder and are arranged lying opposite each other.

5. The port cannula system according to claim 1, wherein the at least two hinges connect the at least two lower holder steps of the lower holder segment to the at least two support pieces.

6. The port cannula system according to claim 1, wherein the at least two support pieces and the cannula holder are produced by injection molding.

7. The port cannula system according to claim 1, wherein a plurality of grooves are incorporated on at least an underside of the support piece.

8. The port cannula system according to claim 1, wherein a padding is arranged on at least an underside of the at least two support pieces.

9. The port cannula system according to claim 1, wherein an underside of the at least two support pieces are covered at least in part with a layer of an adhesive for releasably connecting the at least two support pieces to the patient's skin.

10. The port cannula system according to claim 1, wherein the feeder is secured on the cannula holder.

11. The port cannula system according to claim 1, wherein the cannula holder has at least one middle holder segment connected to the lower holder segment, and an upper holder segment connected to the middle holder segment.

12. The port cannula system according to claim 1, wherein the cannula holder comprises a grip piece and an upper holder segment, the grip piece being connected to at least one of the upper holder segment and the feeder.

13. The port cannula system according to claim 1, further comprising an upper holder segment and at least one middle holder segment, wherein the upper holder segment, at least one middle holder segment and the lower holder segment are telescopically movable relative to one another and guided with respect to one another, wherein the upper holder segment, at least one middle holder segment and the lower holder segment are pushed at least partially into one another in the puncture position and are drawn apart from one another in the retracted protection position.

14. A kit comprising a port cannula system according to claim 1, an adhesive tape for securing the port cannula system on the patient's skin, a compress for positioning between the port cannula system and the patient's skin, a needle protection cap that can be mounted or is mounted on the cannula, a hose that is connected or can be connected to the feeder, and a hose clamp that is connected or can be connected to the hose.

15. The port cannula system according to claim 2, wherein the at least two hinges are film hinges.

16. The port cannula system according to claim 15, wherein the lower holder segment is connected to the at least two support piece pieces through the at least two lower holder steps, such that the lower holder segment is configured to be spaced from the patient's skin.

17. The port cannula system according to claim 2, wherein the at least two support pieces extend laterally outward from the cannula holder and are arranged lying opposite each other.

18. The port cannula system according to claim 1, wherein the cannula holder comprises the lower holder segment, which is connected to the at least two support pieces through the at least two lower holder steps, such that the lower holder segment is configured to be spaced from the patient's skin.

19. The port cannula system of claim 1, wherein the stationary one-part lower holder segment comprising the at least two lower holder steps extending from the plate and connected to the at least two support pieces comprises: a telescopic segment positioned on the plate, and two lower holder steps extending from the plate and connected to two support pieces configured to provide the height compensation through pivotable movement of the two support pieces along two hinges to allow leveling of the port cannula system on the uneven regions of the patient' skin to form a space between an underside of the cannula holder and the patient's skin.

20. The port cannula system according to claim 1, wherein the cannula is configured to move via the through-opening of the base plate between the puncture position and the safety position.

21. The port cannula system according to claim 1, wherein the base plate comprises a plate surface surrounding the through-opening, with the plate surface configured to prevent a telescopic structure, coupled to the lower holder segment and moveable in an inner space of the port cannula system defined by at least the lower holder segment, from falling through the through-opening of the base plate.

22. The port cannula system according to claim 21, wherein the telescopic structure comprises an upper holder segment and at least one middle holder segment, wherein the upper holder segment, at least one middle holder segment and the lower holder segment are telescopically movable relative to one another and guided with respect to one another, and wherein the upper holder segment, the at least one middle holder segment and the lower holder segment are pushed at least partially into one another in the puncture position and are drawn apart from one another in the retracted protection position such that, in the retracted position, the cannula tip is positioned within the inner space.

* * * * *